United States Patent
Davies et al.

(10) Patent No.: US 9,717,864 B2
(45) Date of Patent: Aug. 1, 2017

(54) DISPENSE INTERFACE WITH LOCKOUT ELEMENT

(75) Inventors: James Alexander Davies, Warwickshire (GB); Simon Lewis Bilton, Warwickshire (GB); David Moore, Leicestershire (GB); Steven Wimpenny, Warwickshire (GB); Christopher Nigel Langley, Warwickshire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 210 days.

(21) Appl. No.: 14/113,535

(22) PCT Filed: Apr. 26, 2012

(86) PCT No.: PCT/EP2012/057689
§ 371 (c)(1),
(2), (4) Date: Oct. 23, 2013

(87) PCT Pub. No.: WO2012/146675
PCT Pub. Date: Nov. 1, 2012

(65) Prior Publication Data
US 2015/0314082 A1    Nov. 5, 2015

Related U.S. Application Data

(60) Provisional application No. 61/480,063, filed on Apr. 28, 2011.

(30) Foreign Application Priority Data

Jul. 8, 2011    (EP) .................................. 11173276

(51) Int. Cl.
A61M 5/00      (2006.01)
A61M 5/50      (2006.01)
A61M 5/34      (2006.01)
A61M 5/24      (2006.01)
A61M 5/28      (2006.01)

(52) U.S. Cl.
CPC ................ *A61M 5/50* (2013.01); *A61M 5/34* (2013.01); *A61M 5/2448* (2013.01); *A61M 5/284* (2013.01); *A61M 2205/273* (2013.01)

(58) Field of Classification Search
CPC ........ A61M 5/50; A61M 5/34; A61M 5/2448; A61M 5/284; A61M 2205/273;
(Continued)

(56) References Cited

U.S. PATENT DOCUMENTS 5,658,257 A    8/1997  Ryles
2003/0060776 A1  3/2003  Heiniger
(Continued)

FOREIGN PATENT DOCUMENTS

EP    2201975 A1    6/2010
JP    2003525087 A  8/2003
(Continued)

*Primary Examiner* — Edelmira Bosques
*Assistant Examiner* — Leah Swanson
(74) *Attorney, Agent, or Firm* — McDonnell Boehnen Hulbert & Berghoff LLP

(57) ABSTRACT

A dispense interface for use with a drug delivery device with an inner body and with a lockout element. The lockout element is coupled to the inner body movable from a receptive condition to a locked condition, wherein in the receptive condition the dispense interface is attachable to the drug delivery device. In the locked condition, the dispense interface is not-attachable to the drug delivery device. The lockout element is configured to move from the receptive condition to the locked condition when said dispense interface is attached to and detached from said drug delivery device.

20 Claims, 14 Drawing Sheets

(58) Field of Classification Search
CPC .... A61M 5/344; A61M 5/348; A61M 5/5013; A61M 5/504; A61M 5/502; A61M 5/5066; A61M 5/508; A61M 5/5086; A61M 2005/5006; A61M 2005/5026; A61M 2005/5033; A61M 2005/5046; A61M 2005/506; A61M 2005/5073; A61M 2205/27; A61M 2205/276
USPC ....................................................... 604/110
See application file for complete search history.

(56) References Cited

U.S. PATENT DOCUMENTS

| | | | |
|---|---|---|---|
| 2008/0154192 A1* | 6/2008 | Schraga | A61M 5/50 604/110 |
| 2008/0177238 A1 | 7/2008 | Follman et al. | |
| 2010/0114035 A1 | 5/2010 | Schubert et al. | |
| 2012/0150125 A1* | 6/2012 | Karlsson | A61M 5/326 604/198 |

FOREIGN PATENT DOCUMENTS

| | | | | |
|---|---|---|---|---|
| JP | 2008212645 A | 9/2008 | | |
| JP | 2010519989 A | 6/2010 | | |
| WO | 8806463 A1 | 9/1988 | | |
| WO | 9218186 A1 | 10/1992 | | |
| WO | 9421313 A1 | 9/1994 | | |
| WO | WO 2010147552 A1 * | 12/2010 | | A61M 5/326 |

\* cited by examiner

DISPENSE INTERFACE WITH LOCKOUT ELEMENT

CROSS REFERENCE TO RELATED APPLICATIONS

The present application is a U.S. National Phase application pursuant to 35 U.S.C. §371 of International Application No. PCT/EP2012/057689 filed Apr. 26, 2012, which claims priority to U.S. Provisional Patent Application No. 61/480,063, filed Apr. 28, 2011 and European Patent Application No. 11173276.4 filed Jul. 8, 2011. The entire disclosure contents of these applications are herewith incorporated by reference into the present application.

FIELD OF INVENTION

The present patent application relates to medical devices for delivering at least two drug agents from separate reservoirs. Such drug agents may comprise a first and a second medicament. The medical device includes a dose setting mechanism for delivering the drug agents automatically or manually by the user.

BACKGROUND

The medical device can be an injector, for example a hand-held injector, especially a pen-type injector, that is an injector of the kind that provides for administration by injection of medicinal products from one or more multidose cartridges. In particular, the present invention relates to such injectors where a user may set the dose.

The drug agents may be contained in two or more multiple dose reservoirs, containers or packages, each containing independent (single drug compound) or pre-mixed (co-formulated multiple drug compounds) drug agents.

Certain disease states require treatment using one or more different medicaments. Some drug compounds need to be delivered in a specific relationship with each other in order to deliver the optimum therapeutic dose. The present patent application is of particular benefit where combination therapy is desirable, but not possible in a single formulation for reasons such as, but not limited to, stability, compromised therapeutic performance and toxicology.

For example, in some cases it may be beneficial to treat a diabetic with a long acting insulin (also may be referred to as the first or primary medicament) along with a glucagon-like peptide-1 such as GLP-1 or GLP-1 analog (also may be referred to as the second drug or secondary medicament).

SUMMARY

Accordingly, there exists a need to provide devices for the delivery of two or more medicaments in a single injection or delivery step that is simple for the user to perform without complicated physical manipulations of the drug delivery device. The proposed drug delivery device provides separate storage containers or cartridge retainers for two or more active drug agents. These active drug agents are then combined and/or delivered to the patient during a single delivery procedure. These active agents may be administered together in a combined dose or alternatively, these active agents may be combined in a sequential manner, one after the other.

The drug delivery device also allows for the opportunity of varying the quantity of the medicaments. For example, one fluid quantity can be varied by changing the properties of the injection device (e.g., setting a user variable dose or changing the device's "fixed" dose). The second medicament quantity can be changed by manufacturing a variety of secondary drug containing packages with each variant containing a different volume and/or concentration of the second active agent.

The drug delivery device may have a single dispense interface. This interface may be configured for fluid communication with a primary reservoir and with a secondary reservoir of medicament containing at least one drug agent. The drug dispense interface can be a type of outlet that allows the two or more medicaments to exit the system and be delivered to the patient.

The combination of compounds from separate reservoirs can be delivered to the body via a double-ended needle assembly. This provides a combination drug injection system that, from a user's perspective, achieves drug delivery in a manner that closely matches the currently available injection devices that use standard needle assemblies. One possible delivery procedure may involve the following steps:

1. Attach a dispense interface to a distal end of the electro-mechanical injection device. The dispense interface comprises a first and a second proximal needle. The first and second needles pierce a first reservoir containing a primary compound and a second reservoir containing a secondary compound, respectively.

2. Attach a dose dispenser, such as a double-ended needle assembly, to a distal end of the dispense interface. In this manner, a proximal end of the needle assembly is in fluidic communication with both the primary compound and secondary compound.

3. Dial up/set a desired dose of the primary compound from the injection device, for example, via a graphical user interface (GUI).

4. After the user sets the dose of the primary compound, the micro-processor controlled control unit may determine or compute a dose of the secondary compound and preferably may determine or compute this second dose based on a previously stored therapeutic dose profile. It is this computed combination of medicaments that will then be injected by the user. The therapeutic dose profile may be user selectable. Alternatively, the user can dial or set a desired dose of the secondary compound.

5. Optionally, after the second dose has been set, the device may be placed in an armed condition. The optional armed condition may be achieved by pressing and/or holding an "OK" or an "Arm" button on a control panel. The armed condition may be provided for a predefined period of time during which the device can be used to dispense the combined dose.

6. Then, the user will insert or apply the distal end of the dose dispenser (e.g. a double ended needle assembly) into the desired injection site. The dose of the combination of the primary compound and the secondary compound (and potentially a third medicament) is administered by activating an injection user interface (e.g. an injection button).

Both medicaments may be delivered via one injection needle or dose dispenser and in one injection step. This offers a convenient benefit to the user in terms of reduced user steps compared to administering two separate injections.

Delivering one or more medicaments through a dose dispenser with a dispense interface can result in the contamination of the dispense interface with traces of each medicament. This contamination may prohibit reusing the dispense interface, for example after a certain time or after a predetermined number of usages, because the purity of the delivered medicaments cannot be guaranteed. Even a user who is conscious of this problem may inadvertently try to reuse a dispense interface because he may not remember and may find it difficult or impossible to determine by inspection whether a given dispense interface has in fact been used or not.

It is therefore desirable to provide the dispense interface with a mechanism that prevents reuse of the dispense interface with a drug delivery device. This mechanism should be such that it is effective in its prevention of reuse as well as safe from manual manipulation by a user.

The invention faces the technical problem of providing a dispense interface for use with a drug delivery device which is prevented of being reused after it has already been used with a drug delivery device.

This object has been solved by a dispense interface for use with a drug delivery device with an inner body and with a lockout element, wherein the lockout element is coupled to the inner body, wherein the lockout element is movable from a receptive condition to a locked condition, wherein in the receptive condition the dispense interface is attachable to the drug delivery device, wherein in the locked condition the dispense interface is not-attachable to the drug delivery device and wherein the lockout element is configured to move from the receptive condition to the locked condition when said dispense interface is attached to and detached from said drug delivery device.

The lockout element is arranged in its receptive condition such that it allows attachment of the dispense interface to the drug delivery device. However, the process of attaching the dispense interface to the drug delivery device mechanically moves the lockout element such that, once the dispense interface is detached and thereby is removed from the drug delivery device, the lockout element mechanically blocks a reattachment of the dispense interface to any drug delivery device. Therefore a reuse of the dispense interface is prevented and the risk of contamination from residual drug components within the dispense interface eliminated.

According to an advantageous embodiment of the dispense interface, the lockout element is movable from the receptive condition to an activated condition, wherein in the activated condition the lockout element is configured to move automatically to the locked condition when said dispense interface is detached from said drug delivery device, and wherein the lockout element is configured to move from the receptive condition to the activated condition when said dispense interface is attached to said drug delivery device. This embodiment ensures in a particular safe and reliable manner the lockout element to move from the receptive condition to the locked condition, when said dispense interface is attached to and detached from said drug delivery device.

Preferably, the lockout element has at least a spring element, which is at least partly relaxed in the receptive condition and strained or further strained in the activated condition. Further strained in this context means, that the spring, starting from a condition in which it partly strained, is moved into a condition, in which it is even more tightly strained than in the prior partly strained condition. Also, the spring element is at least partly strained in the locked condition. Accordingly, in the activated and/or the locked condition the spring element stores energy, wherein in the receptive condition the spring element stores less or no energy.

This configuration allows the dispense interface to be manufactured, in particular to be assembled with little effort since the spring element in the originally adjusted receptive condition is not strained. At the same time, energy in the spring element may in a simple manner be built up or increased by attaching the dispense interface to a drug delivery device, whereby the lockout element is moved from the receptive to the activated condition.

In a particularly preferred embodiment, the spring element in the activated condition is more tightly strained than in the locked condition. Accordingly, in the activated condition the spring element stores more energy than in the locked condition. This energy is reliably transformable into movement of the lockout element, especially an automatic movement to the locked condition. In particular, the spring element may effect an automatic movement of the lockout element from the activated to the locked condition.

The spring element may be an integral part of the lockout element or a separate element, which is connected to the lockout element. Further, the spring element may comprise one or more spring arms, wherein the spring element preferably comprises two spring arms. The spring arms may have recesses for receiving portions of the inner body.

It is further preferred, that the lockout element has at least a bearing section for bearing a distal portion of the drug delivery device, wherein in the receptive condition the bearing section is in an initial position, wherein in the locked condition the bearing section is in a displaced position, in which it has been displaced from its initial position, and wherein the bearing section is resiliently supported on the inner body by the spring element. Thereby, it is in a particularly simple manner possible to influence the strain condition of the spring element by attaching the dispense interface to a drug delivery device.

In particular, the lockout element may be configured such that when said dispense interface is attached to said drug delivery device, a distal portion of the drug delivery device acts on said bearing section such that said spring element is strained or further strained. Accordingly, by attaching the dispense interface to the drug delivery device, the energy stored in the spring element is increased. This enables the lockout element to change its condition. In particular, the lockout element may thereby be moved from the receptive condition to the activated condition.

In a further preferred embodiment, the lockout element has a clamping lock and the inner body has a retaining portion, wherein the clamping lock is in a locking engagement with the retaining portion such as to allow the lockout element to be moved into the activated and/or locked condition and such as to prevent the lockout element from being moved back into the receptive condition. Accordingly, the clamping lock allows movement of the lockout element in only one direction and prevents movement in the opposite direction.

Thereby, the lockout element may reliably be maintained in the activated and/or locked condition once it has been moved into the activated and/or locked condition. Thus, any movement to strain or further strain the spring element is irreversible, which ensures that the lockout element is not moved back to the receptive condition. This safely prevents the dispense interface from being reattached to the drug delivery device after it has been used.

It is moreover preferred, that the clamping lock is provided on the bearing section and the clamping lock is in a locking engagement with the retaining portion such as to allow the bearing section to be moved from the initial into the displaced position and such as to prevent the bearing section from being moved back in the direction of the initial position.

Accordingly, by attaching the dispense interface to said drug delivery device, a distal portion of the drug delivery device acts on said bearing section such that said bearing portion is moved into the displaced position. Thus, by detaching the dispense interface from the drug delivery device, the distal portion of the drug delivery device is retracted from the bearing section, wherein the bearing section remains in the displaced position. In particular the locking engagement of the clamping lock prevents the bearing section to be moved back into the initial position. The spring elements therefore remain in their strained condition. Providing the clamping element on the bearing section allows a simple constructive design of the lockout element, while at the same time a reliable locking engagement of the clamping lock is ensured.

Preferably, the clamping lock is configured to allow a stepless locking engagement with the retaining portion. This means, that a locking engagement may be realized at any desired position of the retaining portion. In particular, it is not necessary to induce engagement of the clamping lock with the retaining portion on defined locking sections. Thereby, the lockout element in any position is securely prevented from being moved back in the direction of the receptive condition. Therefore, the bearing section in any position is prevented from being moved in the direction of the initial position. Particularly even very little movements of the lockout element in the direction of the receptive condition may be prevented, whereby the handling properties of the lockout element are improved.

The clamping lock may comprise at least one tooth with an edge, in particular a sharp edge, which tooth engages the retaining portion of the inner body at an angle other than a right angle. Thereby, the tooth may be oriented in the direction, in which movement shall be prevented. Further, the tooth is pivotally arranged to a section of the lockout element and comprises a sharp edge, which is in engagement with the surface of the retaining portion. Thus, forcing the lockout element to move in the direction of the receptive condition, particularly, forcing the bearing section to move in the direction of its initial position causes the tooth to pivotally move and thereby rest with its sharp edge on the surface of the retaining portion even more firmly. Any further movement of the lockout element in the direction of the receptive condition increases this process.

Preferably, the clamping lock comprises more than one tooth, in particular two or four teeth, which may be pairwise arranged on opposite sides, thus increasing the clamping effect.

According to yet another embodiment, the lockout element has at least a blocking element, wherein in the receptive condition the blocking element is in an open position, in which it allows the distal portion of the drug delivery device to approach the inner body, and wherein in the locked condition the blocking element is in a blocking position, in which it prevents the distal portion of the drug delivery device to approach the inner body.

Providing a lockout element with a blocking element allows the reattachment of the dispense interface to be prevented mechanically with a particularly simple constructive design of the lockout element. At the same time the mechanical blocking is reliable and therefore safely prevents the dispense interface from reattachment. The blocking function may be further improved by providing more than one blocking element, in particular two blocking elements.

It is further preferred, that the blocking element in the activated condition is in a strained position, in which it is strained against a support surface of the drug delivery device, such that the blocking element moves automatically into the blocking position when said dispense interface is detached from said drug delivery device.

Accordingly, in the activated condition the blocking element exerts a resilient spring force on the support surface of the drug delivery device, and by detaching the dispense interface from the drug delivery device, the support surface is refracted and said spring force moves the blocking element automatically from the strained position into the blocking position. This automatic movement provides a secure and reliable movement of the lockout element from the activated to the locked condition, whereby the risk of reattachment of the dispense interface is further minimised.

The spring force, which enables the automatic movement, may either result from a resilient bending of the blocking element itself and/or from straining the spring element in at least one of its portions. Thus, the energy stored in the spring element and/or the blocking element itself in the activated condition may in a simple and reliable manner effect the lockout element to move automatically into the locked condition, in which the blocking element is in its blocking position.

Preferably, the blocking element may adjoin the spring element such that the blocking element is movable from the open position to the strained and/or blocking position by straining the spring element. Thereby, the lockout element may be configured such that when said dispense interface is attached to said drug delivery device, a distal portion of the drug delivery device acts on said bearing section such that the spring element is strained or further strained and the blocking element is thereby strained against the support surface of the drug delivery device. This allows the movement of the lockout element from the receptive to the activated condition to be realized in a secure and reliable manner with a simple constructive design of the lockout element.

It is further preferred, that the lockout element is attached to the inner body by a connecting element. The attachment of the lockout element to the inner body may thereby be safely maintained particularly in the locked condition. This prevents an inadvertent removal of the lockout element from the inner body and accordingly further reduces the risk of reattachment of the dispense interface after it has been used.

The connecting element may be formed as an edge section, which is in engagement with a corresponding surface section of the inner body. Likewise the connection section may comprise a recess, through which a protrusion of the inner body at least partially protrudes. The recess may be provided on the bearing section or the spring element. Also, the connection section may be formed by a connecting portion, which is engaged with an undercut of the inner body. In any of the mentioned embodiments of the connecting element, an at least partly positive fit with the inner body may be provided.

The dispense interface may be produced cost effectively, in case the lockout element is formed as one piece. Preferably the lockout element may be formed from metal, particularly from a flat metal. Likewise the lockout element may be formed from plastic material, particularly from a flat plastic material.

The dispense interface is preferably configured to be used in a system together with a drug delivery device, in particular with a drug delivery device mentioned at the beginning, whereby the dispense interface is removably attached to the drug delivery device. Such a system comprising a drug delivery device as well as a dispense interface may be configured as a sales kit. By detaching the dispense interface from the drug delivery device, it may, due to the lockout element moving to the locked condition, not be reattached to the drug delivery device. Thus, the lockout element of the dispense interface is configured to prevent reattachment of the dispense interface to the drug delivery device after removal from the drug delivery device. The risk of contamination from residual drug components within the dispense interface is thus eliminated.

BRIEF DESCRIPTION OF THE DRAWINGS

These as well as other advantages of various aspects of the present invention will become apparent to those of ordinary skill in the art by reading the following detailed description, with appropriate reference to the accompanying drawings, in which.

DETAILED DESCRIPTION

Figure 1:
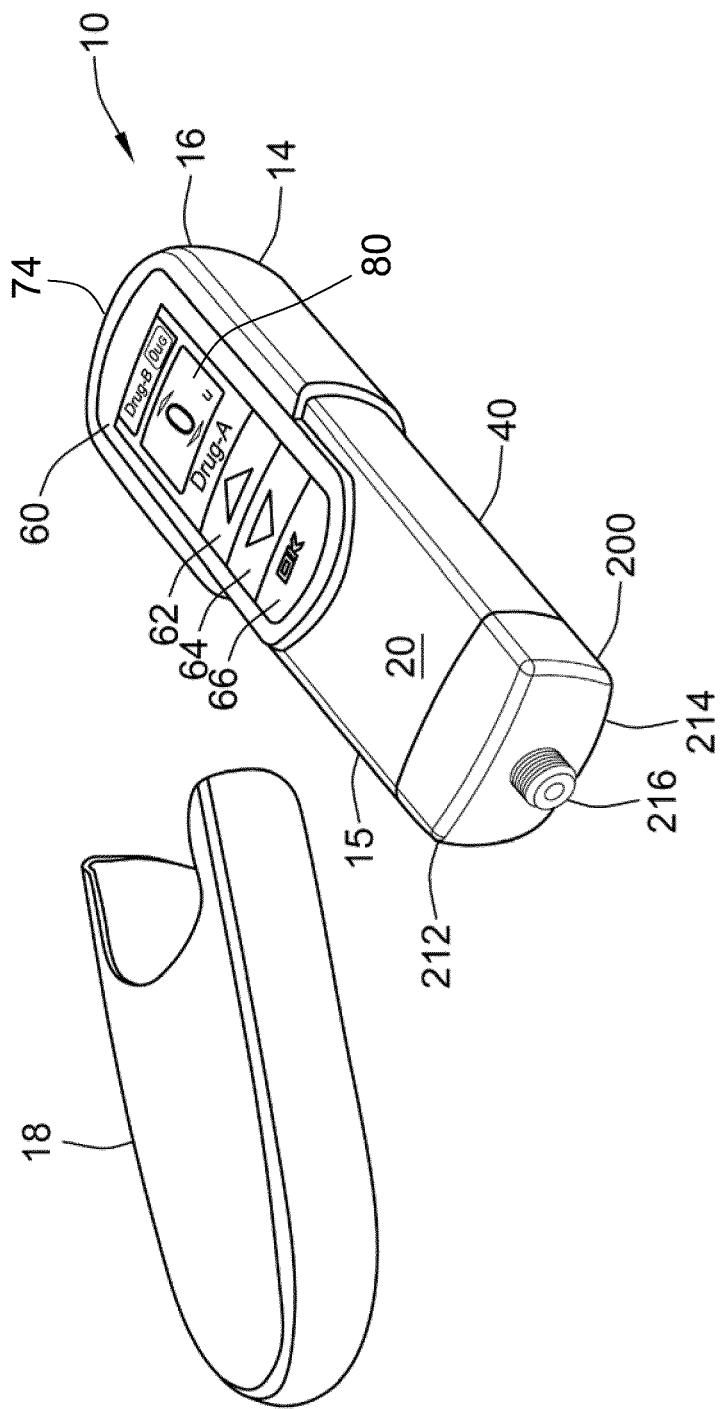
FIG. 1 illustrates a perspective view of a delivery device with an end cap of the device removed.
Figure 2:
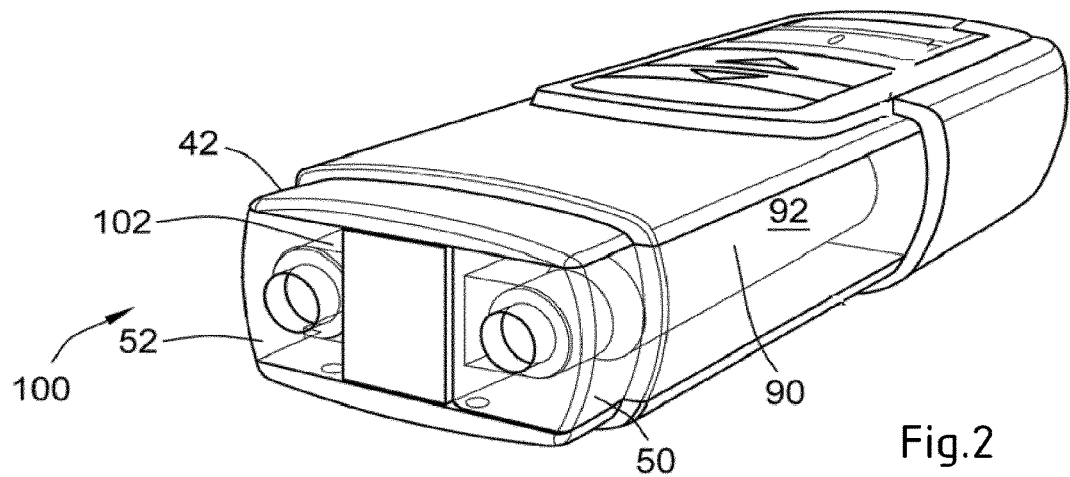
FIG. 2 illustrates a perspective view of the delivery device distal end showing the cartridge.

The drug delivery device illustrated in FIG. 1 comprises a main body 14 that extends from a proximal end 16 to a distal end 15. At the distal end 15, a removable end cap or cover 18 is provided. This end cap 18 and the distal end 15 of the main body 14 work together to provide a snap fit or form fit connection so that once the cover 18 is slid onto the distal end 15 of the main body 14, this frictional fit between the cap and the main body outer surface 20 prevents the cover from inadvertently falling off the main body.

The main body 14 contains a micro-processor control unit, an electro-mechanical drive train, and at least two medicament reservoirs. When the end cap or cover 18 is removed from the device 10 (as illustrated in FIG. 1), a dispense interface 200 is mounted to the distal end 15 of the main body 14, and a dose dispenser (e.g., a needle assembly) is attached to the interface. The drug delivery device 10 can be used to administer a computed dose of a second medicament (secondary drug compound) and a variable dose of a first medicament (primary drug compound) through a single needle assembly, such as a double ended needle assembly.

The drive train may exert a pressure on the bung of each cartridge, respectively, in order to expel the doses of the first and second medicaments. For example, a piston rod may push the bung of a cartridge forward a pre-determined amount for a single dose of medicament. When the cartridge is empty, the piston rod is retracted completely inside the main body 14, so that the empty cartridge can be removed and a new cartridge can be inserted.

A control panel region 60 is provided near the proximal end of the main body 14. Preferably, this control panel region 60 comprises a digital display 80 along with a plurality of human interface elements that can be manipulated by a user to set and inject a combined dose. In this arrangement, the control panel region comprises a first dose setting button 62, a second dose setting button 64 and a third button 66 designated with the symbol "OK." In addition, along the most proximal end of the main body, an injection button 74 is also provided (not visible in the perspective view of FIG. 1).

The cartridge holder 40 can be removably attached to the main body 14 and may contain at least two cartridge retainers 50 and 52. Each retainer is configured so as to contain one medicament reservoir, such as a glass cartridge. Preferably, each cartridge contains a different medicament.

In addition, at the distal end of the cartridge holder 40, the drug delivery device illustrated in FIG. 1 includes a dispense interface 200. As will be described in relation to FIG. 4, in one arrangement, this dispense interface 200 includes a main outer body 212 that is removably attached to a distal end 42 of the cartridge housing 40. As can be seen in FIG. 1, a distal end 214 of the dispense interface 200 preferably comprises a needle hub 216. This needle hub 216 may be configured so as to allow a dose dispenser, such as a conventional pen type injection needle assembly, to be removably mounted to the drug delivery device 10.

Once the device is turned on, the digital display 80 shown in FIG. 1 illuminates and provides the user certain device information, preferably information relating to the medicaments contained within the cartridge holder 40. For example, the user is provided with certain information relating to both the primary medicament (Drug A) and the secondary medicament (Drug B).

Figure 3:
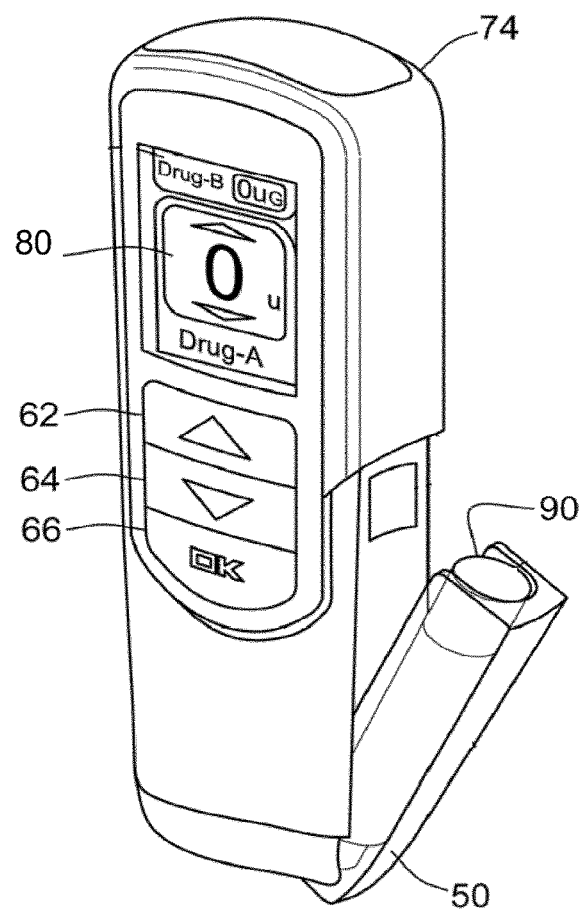
FIG. 3 illustrates a perspective view of the delivery device illustrated in FIG. 1 or 2 with one cartridge retainer in an open position.

As shown in FIG. 3, the first and second cartridge retainers 50, 52 may be hinged cartridge retainers. These hinged retainers allow user access to the cartridges. FIG. 3 illustrates a perspective view of the cartridge holder 40 illustrated in FIG. 1 with the first hinged cartridge retainer 50 in an open position. FIG. 3 illustrates how a user might access the first cartridge 90 by opening up the first retainer 50 and thereby having access to the first cartridge 90.

Figure 4:
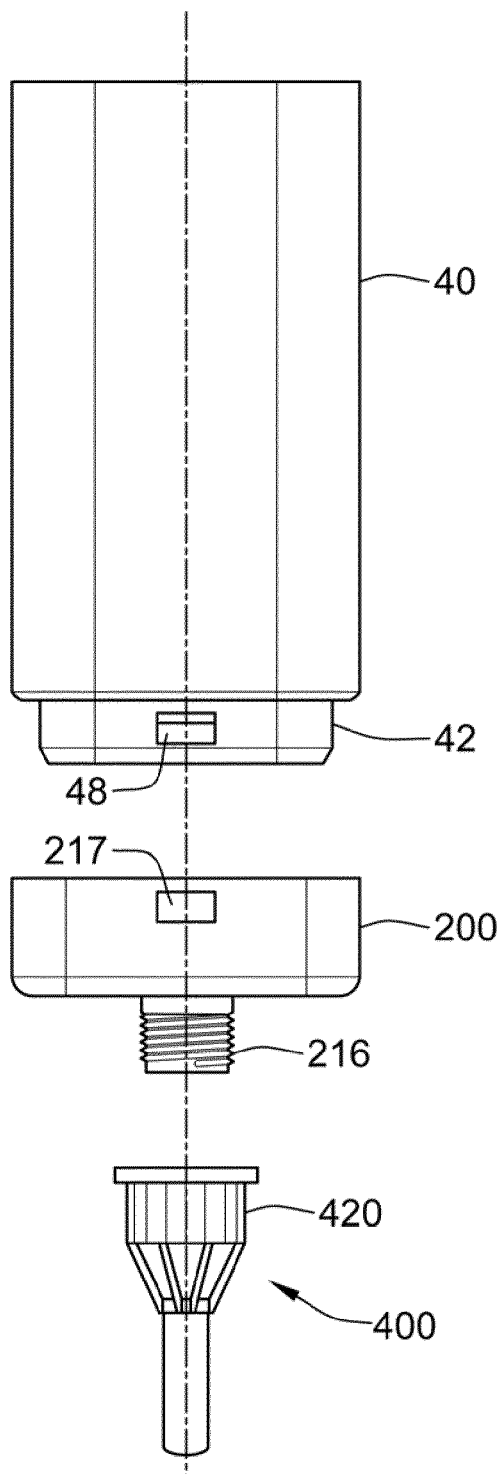
FIG. 4 illustrates a dispense interface and a dose dispenser that may be removably mounted on a distal end of the delivery device illustrated in FIG. 1.

As mentioned above when discussing FIG. 1, a dispense interface 200 is coupled to the distal end of the cartridge holder 40. FIG. 4 illustrates a flat view of the dispense interface 200 unconnected to the distal end of the cartridge holder 40. A dose dispenser or needle assembly that may be used with the interface 200 is also illustrated and is provided in a protective outer cap 420.

Figure 5:
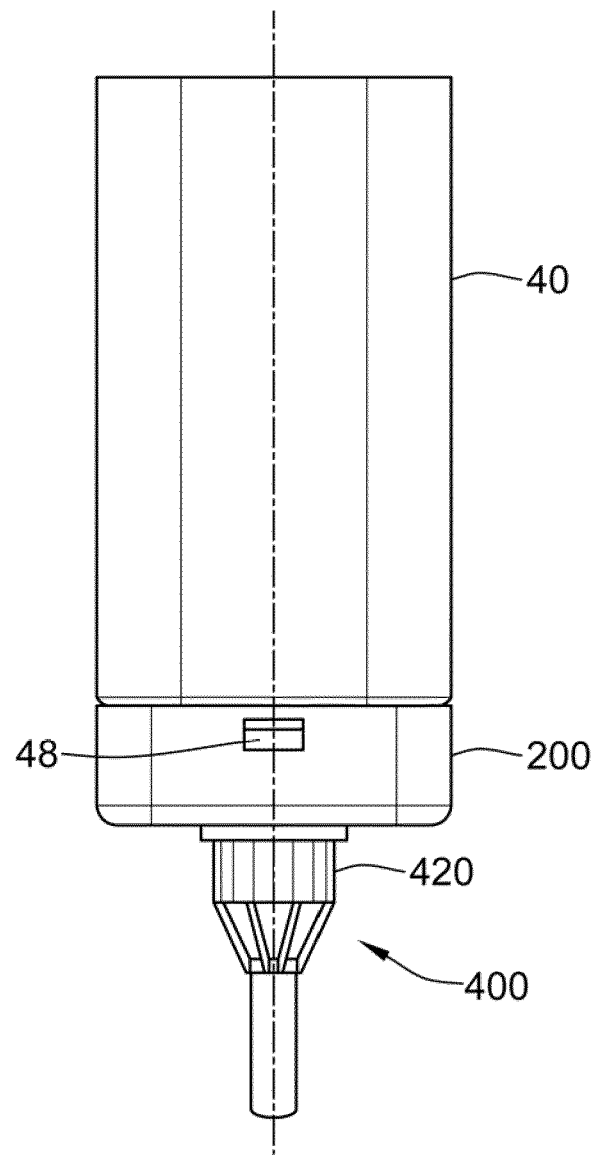
FIG. 5 illustrates the dispense interface and the dose dispenser illustrated in FIG. 4 mounted on a distal end of the delivery device illustrated in FIG. 1.

In FIG. 5, the dispense interface 200 illustrated in FIG. 4 is shown coupled to the cartridge holder 40. The axial attachment means between the dispense interface 200 and the cartridge holder 40 can be any known axial attachment means to those skilled in the art, including snap locks, snap fits, snap rings, keyed slots, and combinations of such connections. The connection or attachment between the dispense interface and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate secondary cartridge to a non-matching injection device.

Figure 6:
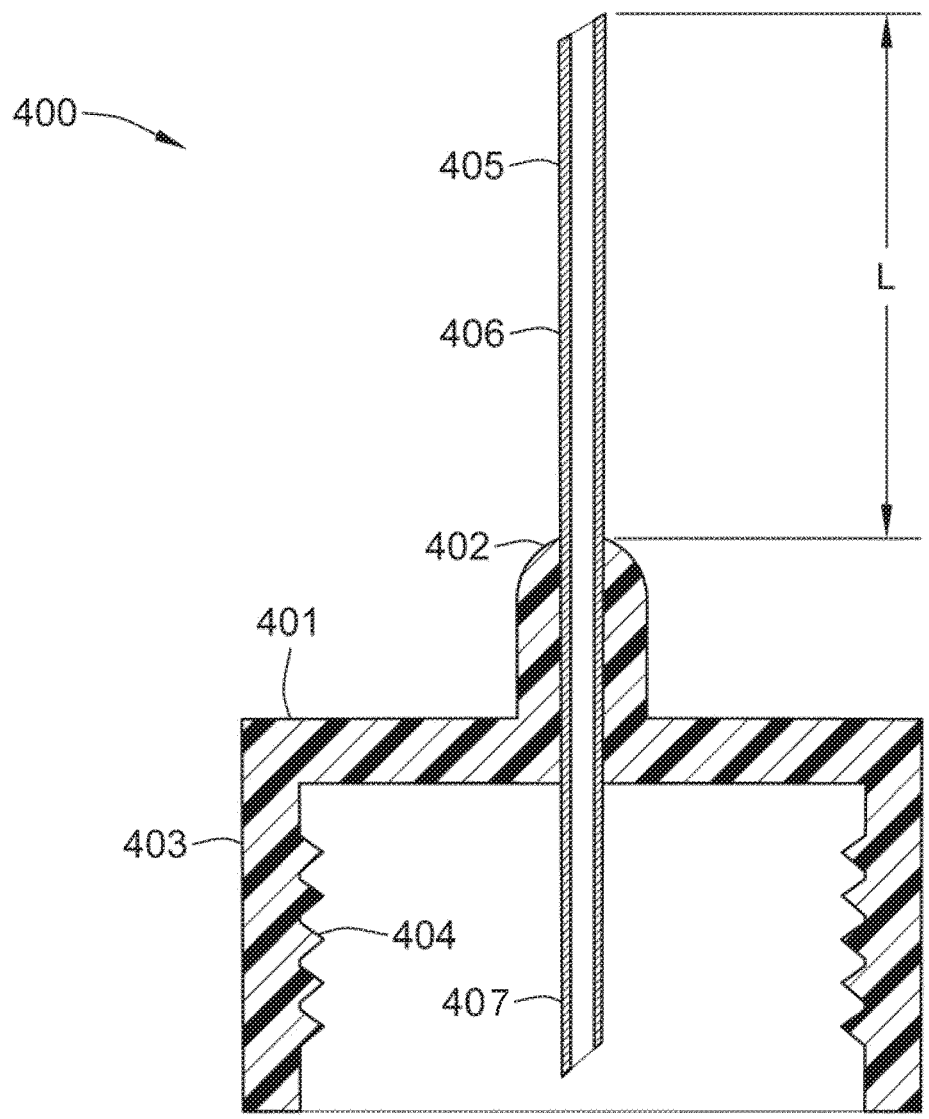
FIG. 6 illustrates one arrangement of a needle assembly that may be mounted on a distal end of the delivery device.
Figure 7:
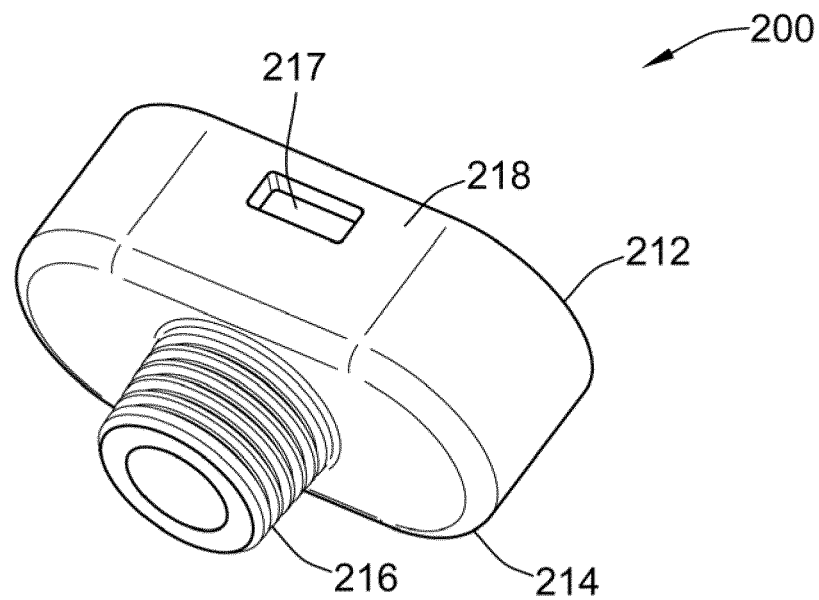
FIG. 7 illustrates a perspective view of the dispense interface illustrated in FIG. 4.

FIG. 5 also illustrates the needle assembly 400 and protective cover 420 coupled to the distal end of the dispense interface 200 that may be screwed onto the needle hub of the interface 200. FIG. 6 illustrates a cross sectional view of the double ended needle assembly 400 mounted on the dispense interface 200 in FIG. 5.

The needle assembly 400 illustrated in FIG. 6 comprises a double ended needle 406 and a hub 401. The double ended needle or cannula 406 is fixedly mounted in a needle hub 401. This needle hub 401 comprises a circular disk shaped element which has along its periphery a circumferential depending sleeve 403. Along an inner wall of this hub member 401, a thread 404 is provided. This thread 404 allows the needle hub 401 to be screwed onto the dispense interface 200 which, in one preferred arrangement, is provided with a corresponding outer thread along a distal hub. At a center portion of the hub element 401 there is provided a protrusion 402. This protrusion 402 projects from the hub in an opposite direction of the sleeve member. A double ended needle 406 is mounted centrally through the protrusion 402 and the needle hub 401. This double ended needle 406 is mounted such that a first or distal piercing end 405 of the double ended needle forms an injecting part for piercing an injection site (e.g., the skin of a user).

Similarly, a second or proximal piercing end 407 of the needle assembly 400 protrudes from an opposite side of the circular disc so that it is concentrically surrounded by the sleeve 403. In one needle assembly arrangement, the second or proximal piercing end 407 may be shorter than the sleeve 403 so that this sleeve to some extent protects the pointed end of the back sleeve. The needle cover cap 420 illustrated in FIGS. 4 and 5 provides a form fit around the outer surface 403 of the hub 401.

Referring now to FIGS. 4 to 11, one preferred arrangement of this interface 200 will now be discussed. In this one preferred arrangement, this interface 200 comprises:
 a main outer body 210,
 an first inner body 220,
 a second inner body 230,
 a first piercing needle 240,
 a second piercing needle 250,
 a valve seal 260, and
 a septum 270.

The main outer body 210 comprises a main body proximal end 212 and a main body distal end 214. At the proximal end 212 of the outer body 210, a connecting member is configured so as to allow the dispense interface 200 to be attached to the distal end of the cartridge holder 40. Preferably, the connecting member is configured so as to allow the dispense interface 200 to be removably connected the cartridge holder 40. In one preferred interface arrangement, the proximal end of the interface 200 is configured with an upwardly extending wall 218 having at least one recess. For example, as may be seen from FIG. 8, the upwardly extending wall 218 comprises at least a first recess 217 and a second recess 219.

Preferably, the first and the second recesses 217, 219 are positioned within this main outer body wall so as to cooperate with an outwardly protruding member located near the distal end of the cartridge housing 40 of the drug delivery device 10. For example, this outwardly protruding member 48 of the cartridge housing may be seen in FIGS. 4 and 5. A second similar protruding member is provided on the opposite side of the cartridge housing. As such, when the interface 200 is axially slid over the distal end of the cartridge housing 40, the outwardly protruding members will cooperate with the first and second recess 217, 219 to form an interference fit, form fit, or snap lock. Alternatively, and as those of skill in the art will recognize, any other similar connection mechanism that allows for the dispense interface and the cartridge housing 40 to be axially coupled could be used as well.

The main outer body 210 and the distal end of the cartridge holder 40 act to form an axially engaging snap lock or snap fit arrangement that could be axially slid onto the distal end of the cartridge housing. In one alternative arrangement, the dispense interface 200 may be provided with a coding feature so as to prevent inadvertent dispense interface cross use. That is, the inner body of the hub could be geometrically configured so as to prevent an inadvertent cross use of one or more dispense interfaces.

A mounting hub is provided at a distal end of the main outer body 210 of the dispense interface 200. Such a mounting hub can be configured to be releasably connected to a needle assembly. As just one example, this connecting means 216 may comprise an outer thread that engages an inner thread provided along an inner wall surface of a needle hub of a needle assembly, such as the needle assembly 400 illustrated in FIG. 6. Alternative releasable connectors may also be provided such as a snap lock, a snap lock released through threads, a bayonet lock, a form fit, or other similar connection arrangements.

The dispense interface 200 further comprises a first inner body 220. Certain details of this inner body are illustrated in FIG. 8-11. Preferably, this first inner body 220 is coupled to an inner surface 215 of the extending wall 218 of the main outer body 210. More preferably, this first inner body 220 is coupled by way of a rib and groove form fit arrangement to an inner surface of the outer body 210. For example, as can be seen from FIG. 9, the extending wall 218 of the main outer body 210 is provided with a first rib 213a and a second rib 213b. This first rib 213a is also illustrated in FIG. 10. These ribs 213a and 213b are positioned along the inner surface 215 of the wall 218 of the outer body 210 and create a form fit or snap lock engagement with cooperating grooves 224a and 224b of the first inner body 220. In a preferred arrangement, these cooperating grooves 224a and 224b are provided along an outer surface 222 of the first inner body 220.

Figure 8:
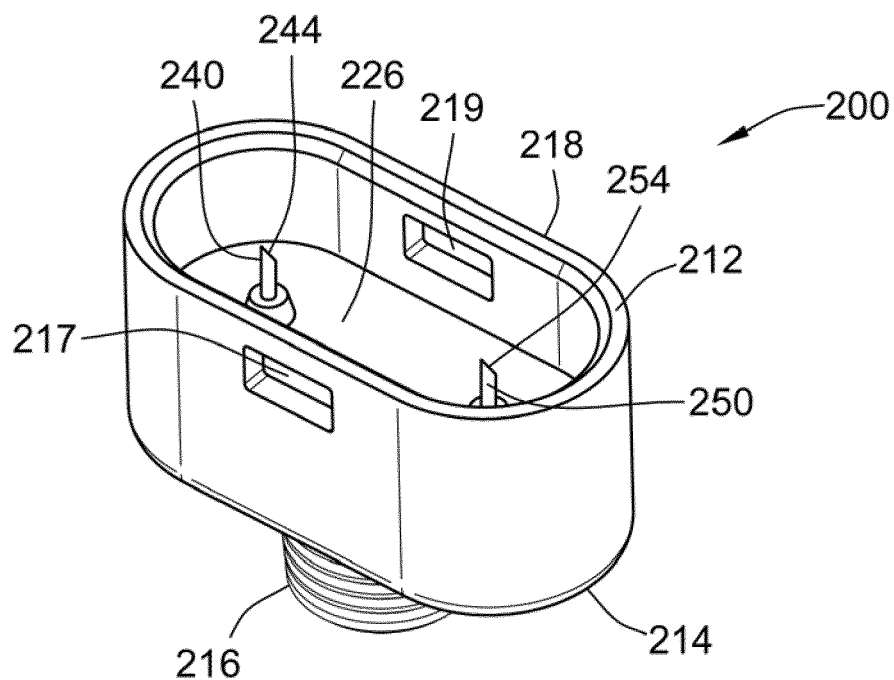
FIG. 8 illustrates another perspective view of the dispense interface illustrated in FIG. 4.
Figure 9:
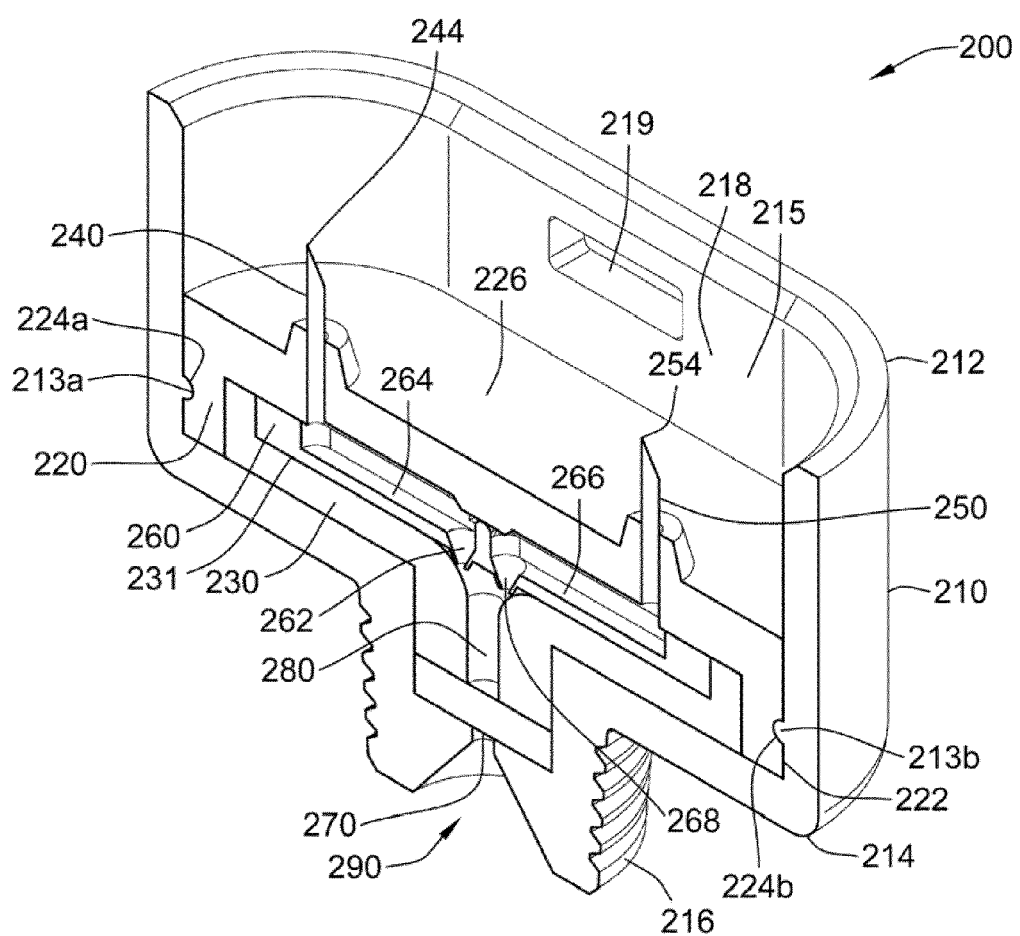
FIG. 9 illustrates a cross-sectional view of the dispense interface illustrated in FIG. 4.
Figure 10:
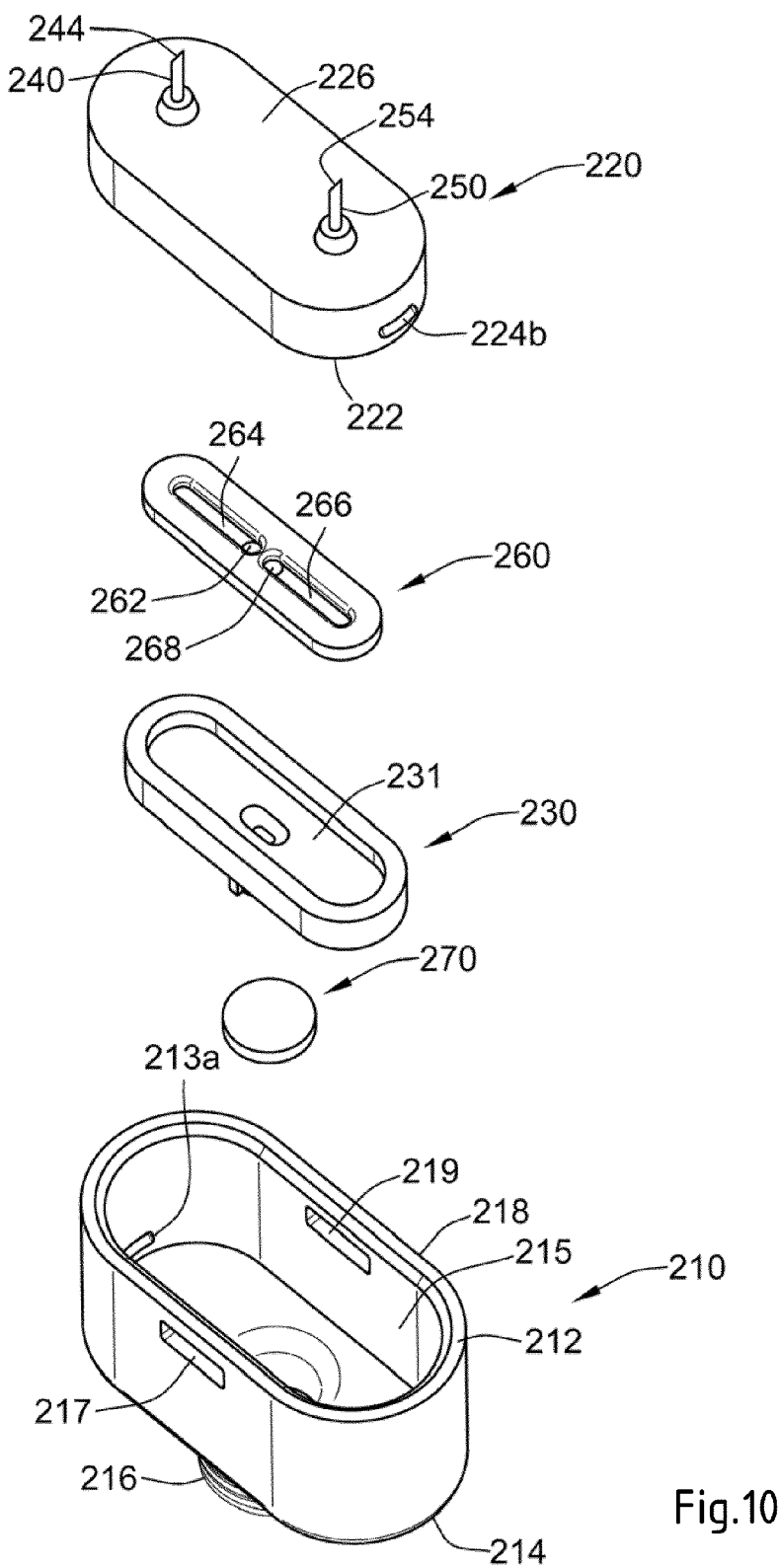
FIG. 10 illustrates an exploded view of the dispense interface illustrated in FIG. 4.

In addition, as can be seen in FIG. 8-10, a proximal surface 226 near the proximal end of the first inner body 220 may be configured with at least a first proximally positioned piercing needle 240 comprising a proximal piercing end portion 244. Similarly, the first inner body 220 is configured with a second proximally positioned piercing needle 250 comprising a proximally piercing end portion 254. Both the first and second needles 240, 250 are rigidly mounted on the proximal surface 226 of the first inner body 220.

Preferably, this dispense interface 200 further comprises a valve arrangement. Such a valve arrangement could be constructed so as to prevent cross contamination of the first and second medicaments contained in the first and second reservoirs, respectively. A preferred valve arrangement may also be configured so as to prevent back flow and cross contamination of the first and second medicaments.

In one preferred system, dispense interface 200 includes a valve arrangement in the form of a valve seal 260. Such a valve seal 260 may be provided within a cavity 231 defined by the second inner body 230, so as to form a holding chamber 280. Preferably, cavity 231 resides along an upper surface of the second inner body 230. This valve seal comprises an upper surface that defines both a first fluid groove 264 and second fluid groove 266. For example, FIG. 9 illustrates the position of the valve seal 260, seated between the first inner body 220 and the second inner body 230. During an injection step, this seal valve 260 helps to prevent the primary medicament in the first pathway from migrating to the secondary medicament in the second pathway, while also preventing the secondary medicament in the second pathway from migrating to the primary medicament in the first pathway. Preferably, this seal valve 260 comprises a first non-return valve 262 and a second non-return valve 268. As such, the first non-return valve 262 prevents fluid transferring along the first fluid pathway 264, for example a groove in the seal valve 260, from returning back into this pathway 264. Similarly, the second non-return valve 268 prevents fluid transferring along the second fluid pathway 266 from returning back into this pathway 266.

Together, the first and second grooves 264, 266 converge towards the non-return valves 262 and 268 respectively, to then provide for an output fluid path or a holding chamber 280. This holding chamber 280 is defined by an inner chamber defined by a distal end of the second inner body both the first and the second non return valves 262, 268 along with a pierceable septum 270. As illustrated, this pierceable septum 270 is positioned between a distal end portion of the second inner body 230 and an inner surface defined by the needle hub of the main outer body 210.

The holding chamber 280 terminates at an outlet port of the interface 200. This outlet port 290 is preferably centrally located in the needle hub of the interface 200 and assists in maintaining the pierceable seal 270 in a stationary position. As such, when a double ended needle assembly is attached to the needle hub of the interface (such as the double ended needle illustrated in FIG. 6), the output fluid path allows both medicaments to be in fluid communication with the attached needle assembly.

The hub interface 200 further comprises a second inner body 230. As can be seen from FIG. 9, this second inner body 230 has an upper surface that defines a recess, and the valve seal 260 is positioned within this recess. Therefore, when the interface 200 is assembled as shown in FIG. 9, the second inner body 230 will be positioned between a distal end of the outer body 210 and the first inner body 220. Together, second inner body 230 and the main outer body hold the septum 270 in place. The distal end of the inner body 230 may also form a cavity or holding chamber that can be configured to be fluid communication with both the first groove 264 and the second groove 266 of the valve seal.

Axially sliding the main outer body 210 over the distal end of the drug delivery device attaches the dispense interface 200 to the multi-use device. In this manner, a fluid communication may be created between the first needle 240 and the second needle 250 with the primary medicament of the first cartridge and the secondary medicament of the second cartridge, respectively.

Figure 11:
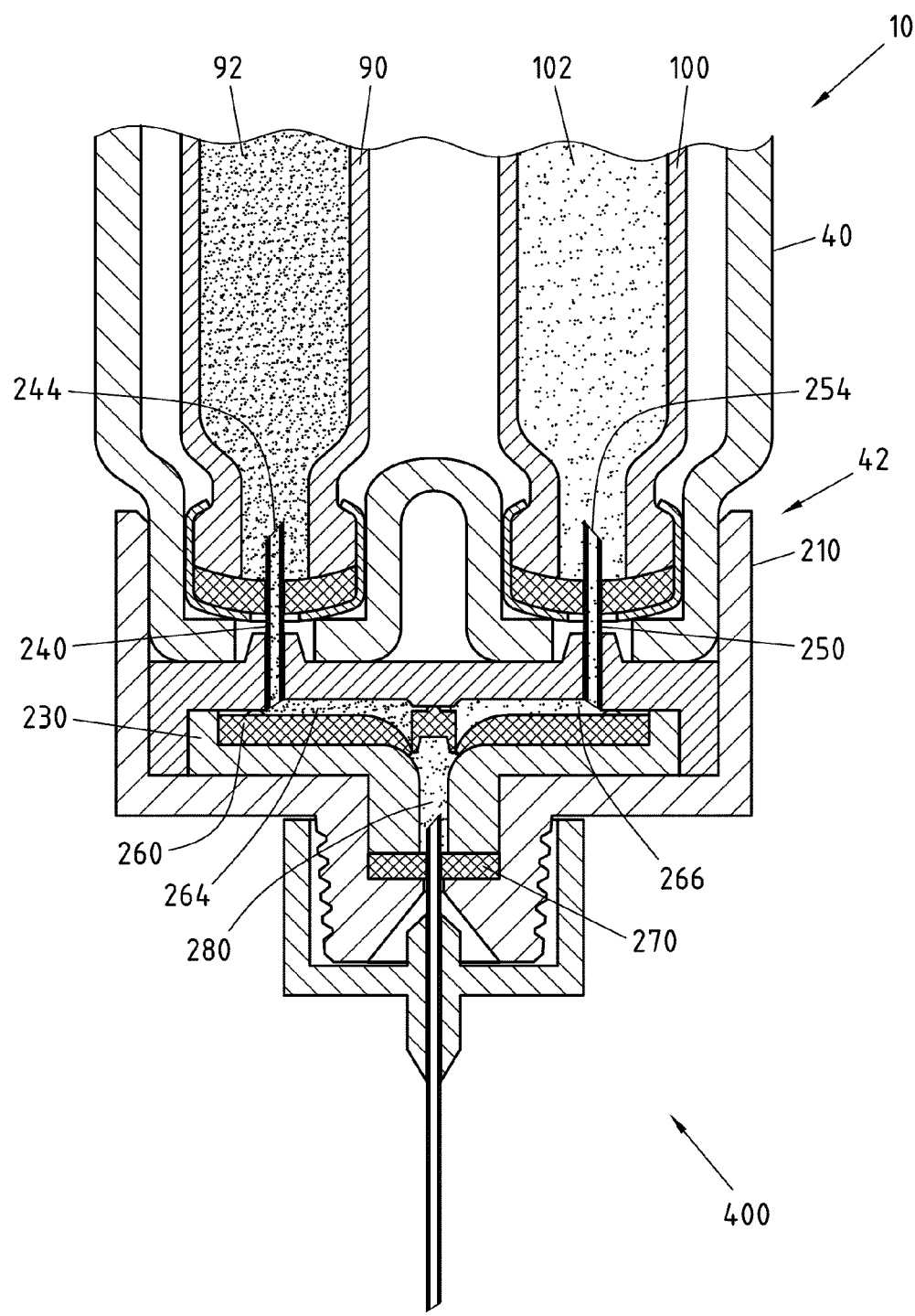
FIG. 11 illustrates a cross-sectional view of the dispense interface and needle assembly mounted onto a drug delivery device, such as the device illustrated in FIG. 1.

FIG. 11 illustrates the dispense interface 200 after it has been mounted onto the distal end 42 of the cartridge holder 40 of the drug delivery device 10 illustrated in FIG. 1. A double ended needle 400 is also mounted to the distal end of this interface. The cartridge holder 40 is illustrated as having a first cartridge containing a first medicament and a second cartridge containing a second medicament.

When the interface 200 is first mounted over the distal end of the cartridge holder 40, the proximal piercing end 244 of the first piercing needle 240 pierces the septum of the first cartridge 90 and thereby resides in fluid communication with the primary medicament 92 of the first cartridge 90. A distal end of the first piercing needle 240 will also be in fluid communication with a first fluid path groove 264 defined by the valve seal 260.

Similarly, the proximal piercing end 254 of the second piercing needle 250 pierces the septum of the second cartridge 100 and thereby resides in fluid communication with the secondary medicament 102 of the second cartridge 100. A distal end of this second piercing needle 250 will also be in fluid communication with a second fluid path groove 266 defined by the valve seal 260.

FIG. 11 illustrates a preferred arrangement of such a dispense interface 200 that is coupled to a distal end 15 of the main body 14 of drug delivery device 10. Preferably, such a dispense interface 200 is removably coupled to the cartridge holder 40 of the drug delivery device 10.

As illustrated in FIG. 11, the dispense interface 200 is coupled to the distal end of a cartridge housing 40. This cartridge holder 40 is illustrated as containing the first cartridge 90 containing the primary medicament 92 and the second cartridge 100 containing the secondary medicament 102. Once coupled to the cartridge housing 40, the dispense interface 200 essentially provides a mechanism for providing a fluid communication path from the first and second cartridges 90, 100 to the common holding chamber 280. This holding chamber 280 is illustrated as being in fluid communication with a dose dispenser. Here, as illustrated, this dose dispenser comprises the double ended needle assembly 400. As illustrated, the proximal end of the double ended needle assembly is in fluid communication with the chamber 280.

In one preferred arrangement, the dispense interface is configured so that it attaches to the main body in only one orientation, that is it is fitted only one way round. As such as illustrated in FIG. 11, once the dispense interface 200 is attached to the cartridge holder 40, the primary needle 240 can only be used for fluid communication with the primary medicament 92 of the first cartridge 90 and the interface 200 would be prevented from being reattached to the holder 40 so that the primary needle 240 could now be used for fluid communication with the secondary medicament 102 of the second cartridge 100. Such a one way around connecting mechanism may help to reduce potential cross contamination between the two medicaments 92 and 102.

Embodiments of a dispense interface with a lockout element and an inner body will be described in detail hereinafter.

Figure 12:
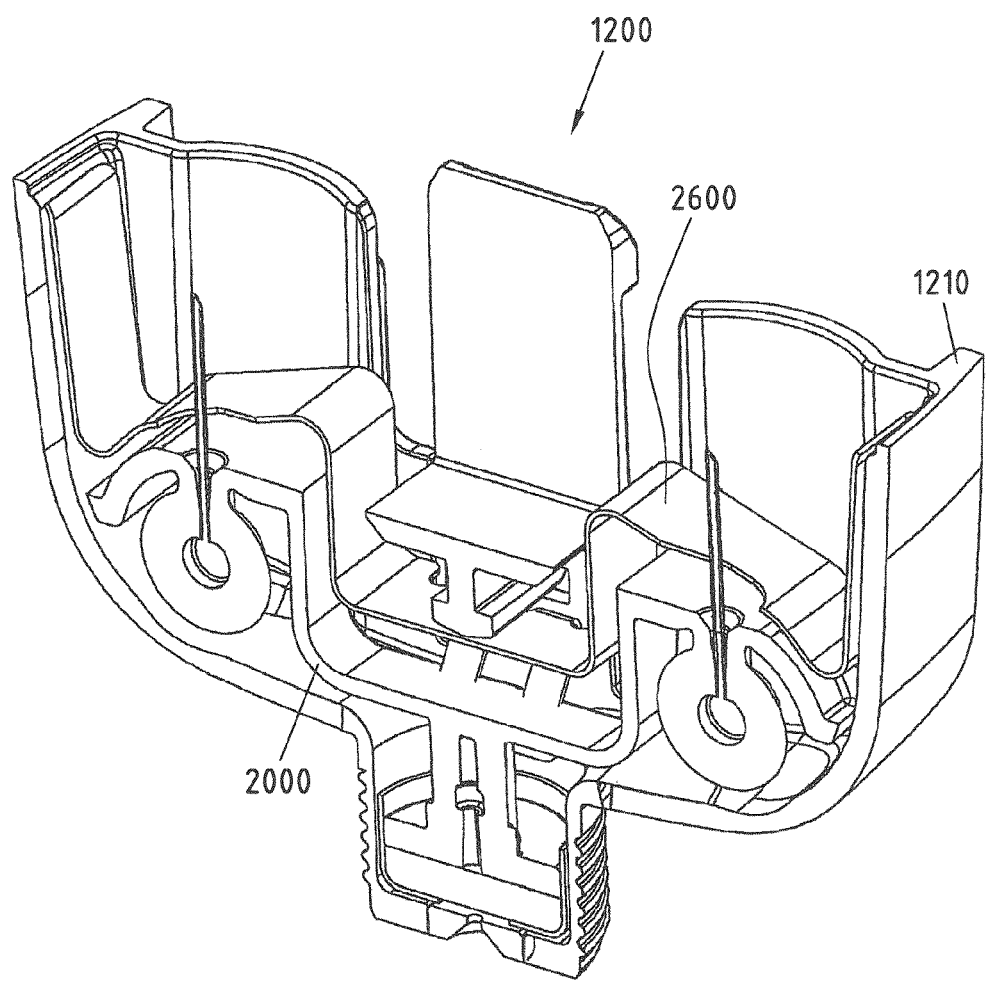
FIG. 12 illustrates a perspective view of the dispense interface with an inner body and a lockout element.
Figure 13:
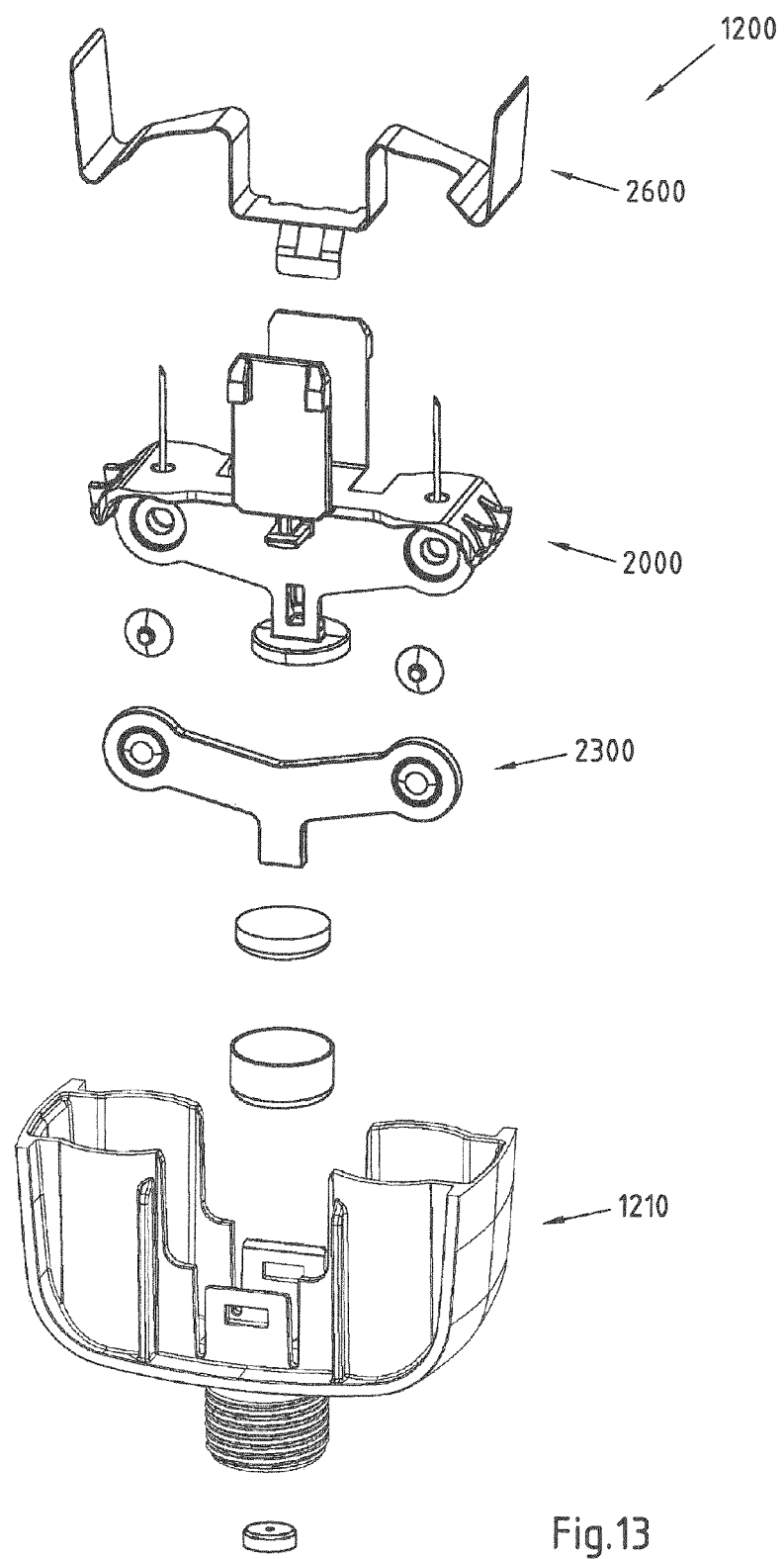
FIG. 13 illustrates an exploded view of the dispense interface illustrated in FIG. 12.

FIGS. 12 and 13 show a dispense interface 1200. As may be seen from FIG. 12 and the exploded view in FIG. 13, the dispense interface 1200 may comprise an outer body 1210 and in inner body 2000. The inner body 2000 may be seated within an interior space defined by the outer main body 1210. Preferably, it is the inner body 2000 of the dispense interface 1200 that is configured to be coupled to a distal end of a drug delivery device while also being securely positioned within an interior space defined by the outer body 1210. The dispense interface 1200 may further comprise a manifold 2300.

As may be further be seen from FIGS. 12 and 13 the dispense interface 2000 also comprises a lockout element in the form of a lockout spring 2600. One reason that a lockout element 2600 may be incorporated into a dispense interface 1200, is to ensure that once the dispense interface 1200 is removed from the drug delivery device, the dispense interface 1200 cannot be re-attached and used a second time. Preventing re-attachment tends to ensure that medicament is not allowed to reside in the dispense interface 1200 indefinitely and contaminate the drug delivered to the patient.

Figure 14:
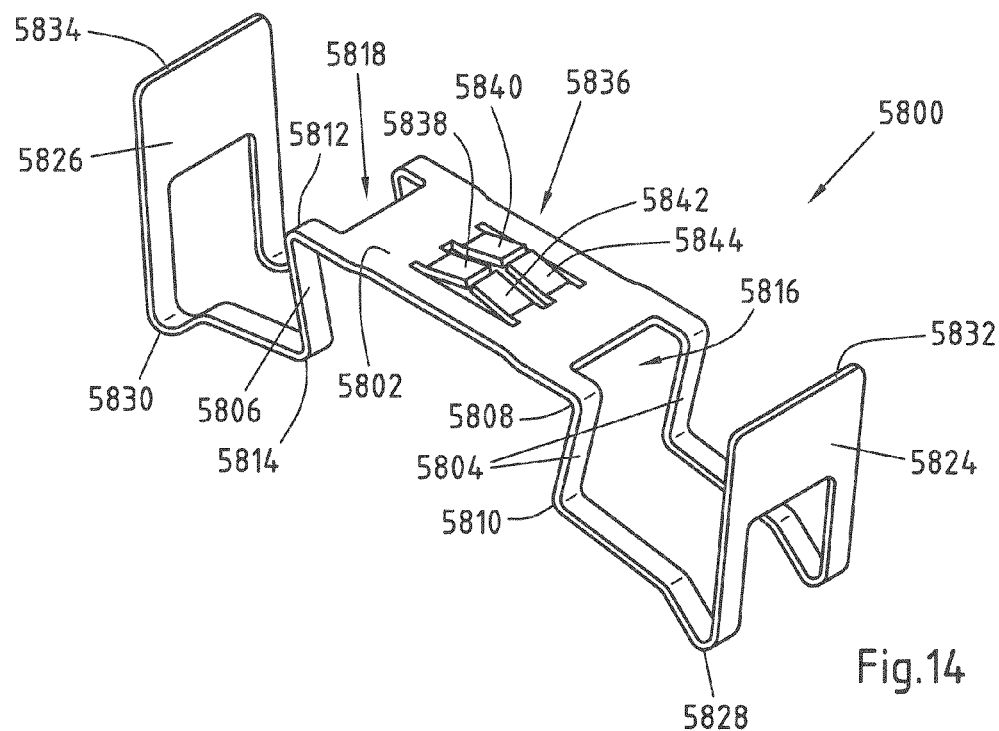
FIG. 14 illustrates a perspective view of a lockout element according to an exemplary embodiment of the invention in the receptive condition.
Figure 15:
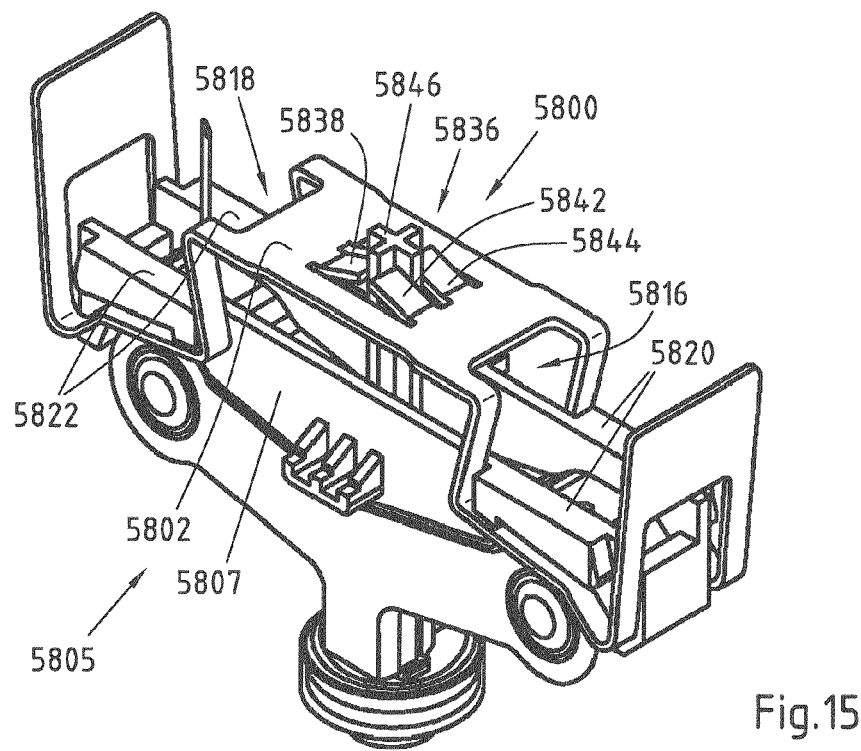
FIG. 15 illustrates a perspective view of the lockout element illustrated in FIG. 14 seated onto in inner body of a dispense interface.

FIG. 14 illustrates a perspective view of an embodiment of a lockout element 5800 according to the invention, and FIG. 15 shows a perspective view of a lockout element 5800 seated onto the inner body 5807 of a dispense interface.

Specifically, FIG. 14 illustrates a perspective view of a lockout element 5800 in the form of a platform spring. The lockout element 5800 is formed as one piece from a flexible material such as a suitable plastic material or a suitable metal material. The lockout element 5800 comprises a bearing section 5802 in the form of a platform, which is configured to bear a distal portion of a drug delivery device, to which the dispense interface may be attached.

The lockout element 5800 further comprises two spring elements 5804 and 5806, which adjoin the bearing section 5802 on opposite sides. The spring elements 5804 and 5806 are formed as spring arms with each two curved sections, wherein the spring element 5804 has a first curved section 5808 and a second curved section 5810 and the spring element 5806 has a first curved section 5812 and a second curved section 5814.

The spring elements 5804 and 5806 each comprise a connecting element in the form of a recess 5816,5818 for connecting the lockout element 5800 to the inner body 5807 of the dispense interface. Thereby the spring element 5804 comprises a recess 5816, wherein spring element 5806 comprises a recess 5818. The recesses 5816 and 5818 may be engaged with corresponding shaped elements, such as protrusions 5820 and 5822 of the inner body 5807. Thereby the lockout element 5800 is securely connected to the inner body 5807, as may be seen in FIG. 15.

Further to this, blocking elements 5824 and 5826 adjoin the ends of the spring elements 5804 and 5806. The transition regions from the spring elements 5804 and 5806 to the respective blocking elements 5824 and 5826 are formed as curved sections 5828 and 5830. The blocking elements 5824 and 5826 may be moved from an open position to a blocking position. In the open position the edges 5832 and 5834 on the free ends of the blocking elements 5824 and 5826 are in a distal position to each other, wherein in the blocking position the edges 5832 and 5834 are approximated to each other, thus blocking the attachment of the dispense interface to a drug delivery device.

In the region of the bearing section 5802, which is formed as a platform, the lockout element 5800 has a clamping lock 5836, which clamping lock 5836 comprises a set of angled teeth 5838,5840,5842,5844. In use, the locking function of the lockout element 5800 may be achieved by the angled teeth 5838,5840,5842,5844 acting along a retaining portion 5846 of the inner body 5807, which may be formed as a cruciform post as illustrated in FIG. 15. As shown, the teeth 5838,5840,5842,5844 are oriented at an angle other than a right angle relative to the corresponding surfaces on the post 5846. In particular, the teeth are oriented in the direction in which movement shall be prevented, thus in a direction facing away from the inner body 5807.

Further, the teeth 5838,5840,5842,5844 are pivotally arranged to the bearing section 5802 of the lockout element 5800 and each comprise a sharp edge at the end, which is in engagement with the surface of the post 5846. The teeth 5838,5840,5842,5844 may be biased in the rearward or proximal direction, facing away from the inner body 5807. Thus the bearing section 5802 may be moved in the direction of the inner body 5807 when the dispense interface 5805 is attached to the drug delivery device, whereby the teeth 5838,5840,5842,5844 slide down the cruciform post 5846 that may be provided on the inner body 5807 of the dispense interface 5805. However, motion of the bearing section 5802 and accordingly the lockout element 5800 in the opposite or proximal direction is prevented. Attempting to produce a rearward motion of the lockout element 5800 will cause the teeth 5838,5840,5842,5844 to pivotally move and thereby bite with its sharp edges into the corresponding surfaces on the post 5846 and thereby cause a locking.

Once displaced from an initial position, the bearing section 5802 will remain in this displaced position. The lockout element 5800 will remain in an activated and/or locked condition, once it has been moved thereto and thereby prevent reattachment of the dispense interface.

Figure 16:
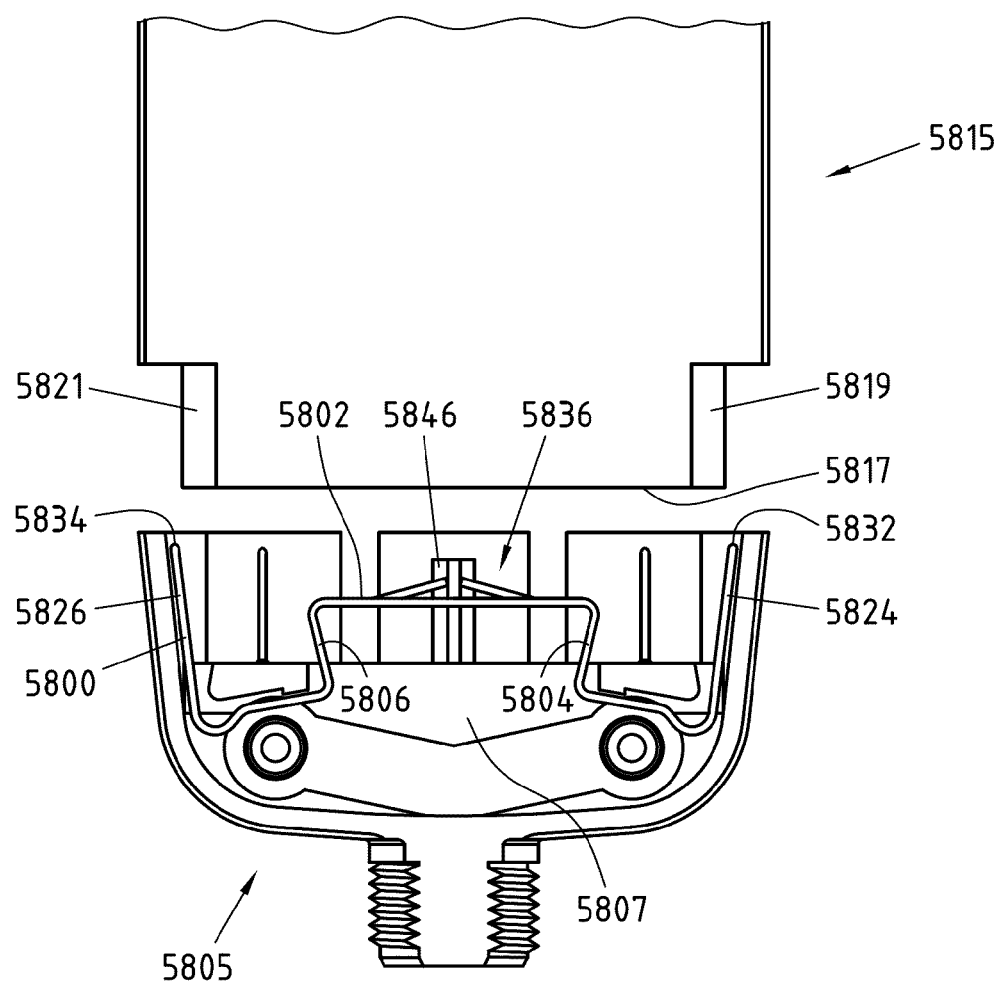
FIG. 16 illustrates a sectional view of a dispense interface with the lockout element illustrated in FIGS. 14 and 15 in a receptive condition.

The perspective views of FIGS. 14 and 15 illustrate the lockout element 5800 in a receptive condition, in which the respective dispense interface is attachable to a drug delivery device. Further FIG. 16 illustrates a cross sectional view of a dispense interface 5805 with a lockout element 5800 in a receptive condition. In this receptive condition, the platform lockout element 5800 is in an unstrained or only slightly strained state on assembly. Thus, the spring arms 5804 and 5806 are in a relaxed condition and thus the blocking elements 5824 and 5826 are in their open position, in which they allow a distal portion 5817 of the drug delivery device 5015 to approach the inner body 5807 of the dispense interface 5805. In the receptive condition, the bearing section 5802 is in an initial position, in which it is positioned distant to the inner body 5807. At the same time the teeth 5838,5840,5842,5844 of the clamping lock 5836 are in locking engagement with the cruciform post 5846 of the inner body 5807.

Figure 17:
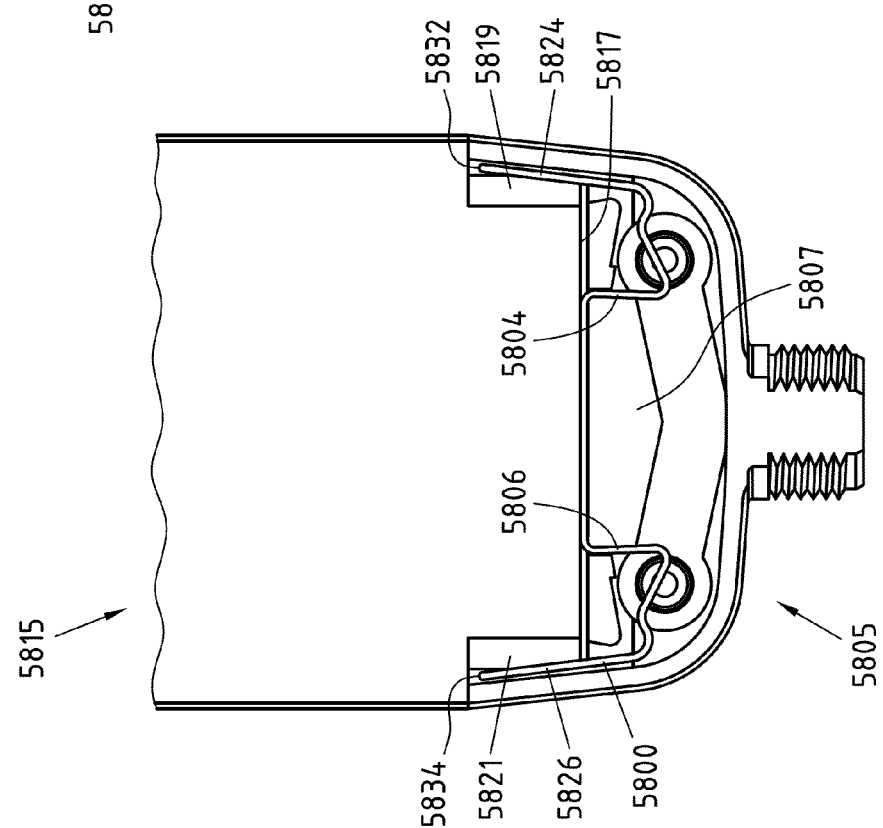
FIG. 17 illustrates a sectional view of a dispense interface with the lockout element illustrated in FIGS. 14 and 15 in an activated condition.

Upon fitting the dispense interface 5805 to the distal end of a drug delivery device 5815, the lockout element 5800 is moved into the activated condition, as shown in the cross-sectional view of FIG. 17. The movement to the activated condition is caused by a distal portion 5817 of the drug delivery device 5815 acting on the bearing section 5802. As illustrated, the bearing section 5802 is thereby displaced from its initial position, and in particular moved in the direction of the inner body 5807.

By moving the bearing section 5802 in the direction of the inner body 5807 the spring elements 5804 and 5806 are strained, while at the same time any movement of the bearing section 5802 back into the initial direction is prevented by the locking engagement of the clamping lock 5836 as well as the distal portion 5817 of the drug delivery device 5815 acting on the bearing section 5802. Furthermore, by straining the spring elements 5804 and 5806, the blocking elements 5824 and 5826 are strained against corresponding support surfaces 5819 and 5821 provided on or near the distal end of the drug delivery device 5815. Thus, the blocking elements 5824 and 5826 in the activated condition act with a resilient spring force on the support surfaces 5819 and 5821. This spring force results from bending portions of the blocking elements 5824 and 5826 themselves and likewise from bending portions of the spring elements 5804 and 5806. The blocking elements 5824 and 5826 remain strained as long as the dispense interface 5805 remains attached to the drug delivery device 5815.

Figure 18:
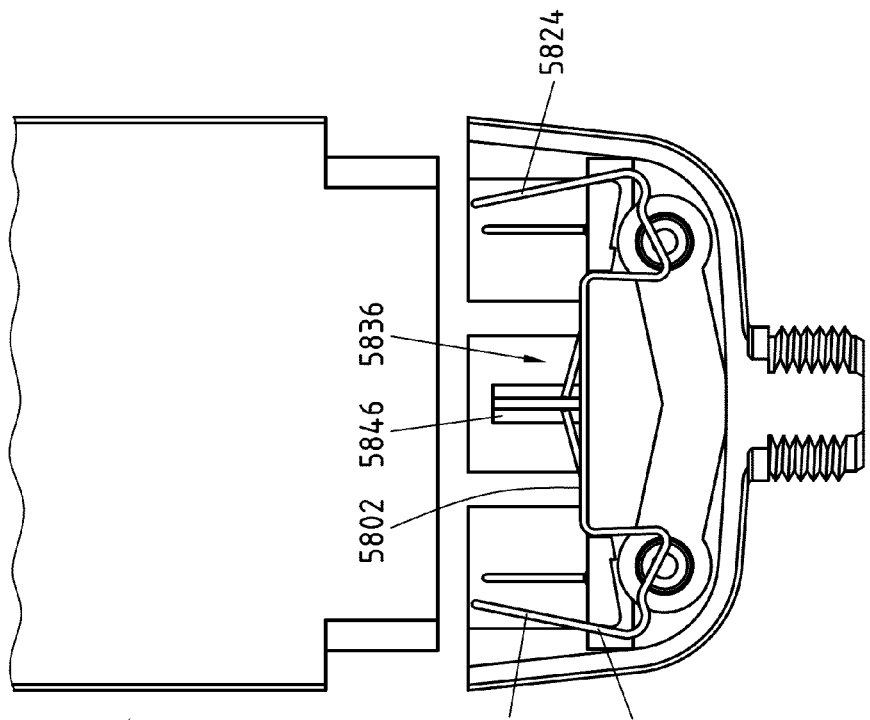
FIG. 18 illustrates a sectional view of a dispense interface with the lockout element illustrated in FIGS. 14 and 15 in a locked condition.

When the dispense interface 5805 is detached from the drug delivery device, the lockout element 5800 is moved into the locked condition, which is illustrated in FIG. 18. In particular, by detaching the dispense interface 5805 from the drug delivery device 5815, the distal portion 5817 of the drug delivery device 5815 is retracted from the bearing section 5802. Since in the activated condition of the lockout element 5800 the bearing section 5802 is prevented from being moved back into the initial position due to a locking engagement of the clamping lock 5836, the spring elements 5804 and 5806 remain strained even after the distal portion 5817 of the drug delivery device 5815 has been retracted from the bearing section 5802.

At the same time the blocking elements 5824 and 5826, as illustrated in FIG. 18, move automatically into a blocking position due to their previously strained condition. This self acting movement may be caused by the relaxing of portions of the blocking elements 5824 and 5826 themselves and likewise by the relaxing of portions of the spring elements 5804 and 5806. In this blocking position, the ends of blocking elements 5824 and 5826 are closer together than in the open receptive condition. In this blocking position, the distance between the ends 5824 and 5826 is less than the width of the distal portion 5817 of the device, thus preventing reattachment.

Since also a complete relaxing of the spring elements 5804 and 5806 is prevented due to the locking engagement of the clamping lock 5836, the blocking elements 5824 and 5826 may not be moved back into and maintained in an open position. Thus, the lockout element 5800 is prevented from being moved back to the receptive condition, whereby it is ensured that the dispense interface 5805 is not reattached to a drug delivery device after it has been used.

In an example embodiment, the blocking elements 5824 and 5826 extend beyond the end of the piercing needles in the blocking position, thus covering the end of the piercing needles at least partially in order to reduce the risk of injury, for example of piercing a finger tip with the end of one of the piercing needles.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta¬ decanoyl) human insulin.

Exendin-4 for example means Exendin-4(1-39), a peptide of the sequence

H His-Gly-Glu-Gly-Thr-Phe-Thr-Ser-Asp-Leu-Ser-Lys-

Gln-Met-Glu-Glu-Glu-Ala-Val-Arg-Leu-Phe-Ile-Glu-

Trp-Leu-Lys-Asn-Gly-Gly-Pro-Ser-Ser-Gly-Ala-Pro-

Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39), des Pro36 [Met(O)14 Trp(O2)25, Asp28] Exendin-4(1-39), des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence

H-(Lys)6-des Pro36 [Asp28] Exendin-4(1-39)-Lys6-NH2, des Asp28 Pro36, Pro37, Pro38Exendin-4(1-39)-NH2, H-(Lys)6-des Pro36, Pro38 [Asp28] Exendin-4(1-39)-NH2, H-Asn-(Glu)5des Pro36, Pro37, Pro38 [Asp28] Exendin-4(1-39)-NH2, des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two 0 sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates

The invention claimed is:

1. Dispense interface for use with a drug delivery device comprising:
    an inner body and
    a lockout element,
    wherein the lockout element is coupled to the inner body,
    wherein the lockout element is movable from a receptive condition to a locked condition,
    wherein in the receptive condition the dispense interface is attachable to the drug delivery device,
    wherein in the locked condition the dispense interface is not attachable to the drug delivery device,
    wherein the lockout element is configured to move from the receptive condition to the locked condition when said dispense interface is attached to and detached from said drug delivery device,
    wherein the lockout element comprises a bearing section and a clamping lock,
    wherein the dispense interface is configured such that a distal portion of the drug delivery device acts on the bearing section to move the bearing section distally relative to the inner body during attachment of the dispense interface to the drug delivery device,
    wherein the inner body comprises a retaining portion,
    wherein the clamping lock is in a locking engagement with the retaining portion such as to allow the lockout element to be moved into the locked condition and such as to prevent the lockout element from being moved back into the receptive condition, and
    wherein the retaining portion is a post extending proximally from the inner body, and wherein the locking engagement of the clamping lock and the retaining portion (i) allows the lockout element to move distally along the post and (ii) prevents the lockout element from moving proximally along the post.

2. The dispense interface according to claim 1,
    wherein the lockout element is movable from the receptive condition to an activated condition,
    wherein in the activated condition the lockout element is configured to move to the locked condition when said dispense interface is detached from said drug delivery device, and
    wherein the lockout element is configured to move from the receptive condition to the activated condition when said dispense interface is attached to said drug delivery device.

3. The dispense interface according to claim 2, wherein the distal movement of the bearing section causes the lockout element to move from the receptive condition to the activated condition.

4. The dispense interface according to claim 2, wherein the lockout element is configured such that (i) attaching the dispense interface to the drug delivery device causes the lockout element to move from the receptive condition to the activated condition, and (ii) detaching the dispense interface from the drug delivery device causes the lockout element to move from the activated condition to the locked condition.

5. The dispense interface according to claim 1, wherein the lockout element comprises at least a spring element, which is at least partly relaxed in the receptive condition and strained or further strained in the activated condition.

6. The dispense interface according to claim 5, wherein the spring element is at least partly strained in the locked condition.

7. The dispense interface according to claim 6,
    wherein the lockout element comprises at least the bearing section configured to bear on the distal portion of the drug delivery device,
    wherein in the receptive condition the bearing section is in an initial position,
    wherein in the locked condition the bearing section is in a displaced position, in which it has been displaced from its initial position, and
    wherein the bearing section is resiliently supported on the inner body by the spring element.

8. The dispense interface according to claim 7, wherein the lockout element is configured such that when said dispense interface is attached to said drug delivery device, a distal portion of the drug delivery device acts on said bearing section such that said spring element is strained or further strained.

9. The dispense interface according to claim 1,
    wherein the clamping lock is provided on the bearing section, and
    wherein the clamping lock is in a locking engagement with the retaining portion such as to allow the bearing section to be moved from the initial into the displaced position and such as to prevent the bearing section from being moved back in the direction of the initial position.

10. The dispense interface according to claim 1, wherein the clamping lock is configured to allow a stepless locking engagement with the retaining portion.

11. The dispense interface according to claim 1,
wherein the lockout element comprises at least a blocking element,
wherein in the receptive condition the blocking element is in an open position, in which it allows the distal portion of the drug delivery device to approach the inner body, and
wherein in the locked condition the blocking element is in a blocking position, in which it prevents the distal portion of the drug delivery device from approaching the inner body.

12. The dispense interface according to claim 11, wherein in the activated condition the blocking element is in a strained position, in which it is strained against a support surface of the drug delivery device such that the blocking element moves automatically into the blocking position when said dispense interface is detached from said drug delivery device.

13. The dispense interface according to claim 11, wherein the blocking element adjoins a spring element such that the blocking element is movable from the open position to the strained position, the blocking position, or both the strained position and the blocking position by straining the spring element.

14. The dispense interface according to claim 11, wherein the at least one blocking element comprises two or more blocking elements, and wherein the bearing section is between the two or more blocking elements.

15. The dispense interface according to claim 1, wherein the lockout element is attached to the inner body by a connecting element.

16. The dispense interface according to claim 1, further comprising an outer body in which the inner body and the locking element are seated, wherein a distal end of the outer body comprises a needle hub configured to removably couple to a needle assembly, and wherein a proximal end of the outer body defines an aperture configured to receive the distal portion of the drug delivery device.

17. An apparatus
comprising a dispense interface according to claim 1 and comprising a drug delivery device,
wherein the dispense interface is removably attached to the drug delivery device.

18. A system comprising
a drug delivery device; and
a dispense interface according to claim 1 configured to be removably attached to the drug delivery device,
wherein the lockout element of the dispense interface is configured to prevent reattachment of the dispense interface to the drug delivery device after removal from the drug delivery device.

19. Dispense interface for use with a drug delivery device comprising:
an inner body and
a lockout element,
wherein the lockout element is coupled to the inner body,
wherein the lockout element is movable from a receptive condition to a locked condition,
wherein in the receptive condition the dispense interface is attachable to the drug delivery device,
wherein in the locked condition the dispense interface is not attachable to the drug delivery device,
wherein the lockout element is configured to move from the receptive condition to the locked condition when said dispense interface is attached to and detached from said drug delivery device,
wherein the lockout element comprises a bearing section and a clamping lock,
wherein the dispense interface is configured such that a distal portion of the drug delivery device acts on the bearing section to move the bearing section distally relative to the inner body during attachment of the dispense interface to the drug delivery device,
wherein the inner body comprises a retaining portion,
wherein the clamping lock is in a locking engagement with the retaining portion such as to allow the lockout element to be moved into the locked condition and such as to prevent the lockout element from being moved back into the receptive condition,
wherein the retaining portion is a post extending proximally from the inner body, and
wherein the clamping lock comprises a plurality of teeth, each tooth having a sharp edge and being angled proximally relative to the post.

20. The dispense interface according to claim 19, wherein the locking engagement of the clamping lock and the retaining portion (i) allows the lockout element to move distally along the post and (ii) prevents the lockout element from moving proximally along the post.

* * * * *